(12) United States Patent
Shekalim et al.

(10) Patent No.: US 8,524,154 B2
(45) Date of Patent: Sep. 3, 2013

(54) SYSTEM AND METHOD FOR PSEUDO-CONTINUOUS MEASUREMENT OF METABOLITE CONCENTRATIONS IN A MAMMALIAN BODY

(75) Inventors: Avraham Shekalim, Nesher (IL); Noam Peleg, Gan-Ner (IL)

(73) Assignee: G-Sense Ltd., Raanana (IL)

( * ) Notice: Subject to any disclaimer, the term of this patent is extended or adjusted under 35 U.S.C. 154(b) by 401 days.

(21) Appl. No.: 12/513,669

(22) PCT Filed: Nov. 8, 2007

(86) PCT No.: PCT/IL2007/001371
§ 371 (c)(1),
(2), (4) Date: May 6, 2009

(87) PCT Pub. No.: WO2008/056363
PCT Pub. Date: May 15, 2008

(65) Prior Publication Data
US 2010/0028208 A1 Feb. 4, 2010

Related U.S. Application Data

(60) Provisional application No. 60/864,978, filed on Nov. 9, 2006.

(51) Int. Cl.
*G01N 21/00* (2006.01)
*F04F 1/00* (2006.01)
*A61M 1/14* (2006.01)
*B67D 7/72* (2010.01)
*G01N 31/00* (2006.01)

(52) U.S. Cl.
USPC ........... 422/63; 422/68.1; 422/81; 422/82.05; 422/500; 422/501; 137/148; 137/154; 137/825; 137/826; 604/38; 604/65; 604/66; 604/67

(58) Field of Classification Search
None
See application file for complete search history.

(56) References Cited

U.S. PATENT DOCUMENTS

| | | | |
|---|---|---|---|
| 3,512,517 A | 5/1970 | Kadish et al. | |
| 4,221,567 A | 9/1980 | Clark et al. | |
| 4,694,832 A | 9/1987 | Ungerstedt | |
| 4,765,339 A | 8/1988 | Jones | |
| 5,193,545 A * | 3/1993 | Marsoner et al. | 600/345 |
| 5,353,792 A | 10/1994 | Lubbers et al. | |
| 5,640,954 A | 6/1997 | Pfeiffer | |
| 6,013,029 A | 1/2000 | Korf et al. | |
| 6,129,702 A * | 10/2000 | Woias et al. | 604/65 |
| 6,572,566 B2 | 6/2003 | Effenhauser | |
| 6,591,126 B2 | 7/2003 | Roeper | |
| 6,852,500 B1 | 2/2005 | Hoss | |
| 7,097,983 B2 | 8/2006 | Markovsky et al. | |

(Continued)

FOREIGN PATENT DOCUMENTS
NL WO9941606 8/1999

*Primary Examiner* — Neil N Turk
(74) *Attorney, Agent, or Firm* — Mark M. Friedman (57) ABSTRACT

A metabolite monitoring system comprising a microdialysis probe including a semi-permeable membrane and a probe flow path passing from an inlet through a sensing volume adjacent to said semi-permeable membrane to an outlet, a fluid delivery device for delivering dialysate to said inlet; and a metabolite monitoring system associated with said outlet for monitoring a concentration of at least one metabolite in said dialysate from said microdialysis probe, wherein said fluid delivery device is configured to deliver a pulsed flow of said dialysate to said inlet.

12 Claims, 8 Drawing Sheets

(56) References Cited

U.S. PATENT DOCUMENTS

| | | |
|---|---|---|
| 7,169,600 B2 | 1/2007 | Hoss |
| 7,291,126 B2 | 11/2007 | Shekalim |
| 2002/0082490 A1* | 6/2002 | Roeper et al. ......... 600/347 |
| 2003/0216683 A1* | 11/2003 | Shekalim ......... 604/67 |
| 2004/0191848 A1* | 9/2004 | Hoss et al. ......... 435/14 |
| 2005/0255442 A1 | 11/2005 | Brassil et al. |
| 2006/0073082 A1* | 4/2006 | Ducree et al. ......... 422/103 |
| 2007/0066877 A1* | 3/2007 | Arnold et al. ......... 600/315 |

* cited by examiner

SYSTEM AND METHOD FOR PSEUDO-CONTINUOUS MEASUREMENT OF METABOLITE CONCENTRATIONS IN A MAMMALIAN BODY

RELATED APPLICATIONS

This patent application is a U.S. National Phase Application of PCT/IL2007/001371 filed on Nov. 8, 2007, and also claims the benefit under 119(e) of U.S. Provisional Patent Application No. 60/864,978 filed Nov. 9, 2006, the contents of which are incorporated herein by reference.

FIELD AND BACKGROUND OF THE INVENTION

The present invention relates to body fluid monitoring and, in particular, it concerns a system and method for pseudo-continuous measurement of metabolite concentrations in a mammalian body, and especially of glucose.

It has been proposed to measure concentrations of a metabolite in a mammalian body by use of a microdialysis probe inserted into the body through which a dialysate passes and absorbs metabolites from the surrounding body fluids. Of particular importance are applications to monitoring of glucose concentrations, which are critical to management of diabetes. Examples of such systems are described in the following U.S. Pat. Nos. 3,512,517; 4,221,567; 4,694,832; 4,765,339; 5,640,954; 6,013,029; and 6,852,500.

Commercial products based upon this technique are plagued by a number of practical problems. Firstly, in order to enhance the concentrations of metabolites in the dialysate, and to minimize the size and weight of fluid reservoirs and pumps of the system, it is preferable to work at very low flow rates. For example, U.S. Pat. No. 6,013,029 refers to flow rates less than 60 micro-liters per hour. In practice, it has been found difficult to achieve and accurately maintain such low flow rates.

Secondly, these systems typically require precise coordinated control of two separate fluid flow rates, a first for the dialysate and a second for a reagent added to the dialysate downstream of the microdialysis probe. For safety reasons, it is considered necessary to add the reagent only after the dialysate has left the part of the probe penetrating into the body. The proportions of these fluids must be maintained exactly constant in order to achieve reliable quantitative measurements. As a result, the pump structure is typically relatively expensive and must be doubled up to regulate both fluids. This requirement for precision is further compounded by the extremely low flow rates mentioned above, together presenting a very serious hurdle to practical implementation of such systems.

Thirdly, and possibly most problematic, the existing systems all suffer from very significant drift in the accuracy of results due to deposition and other interactions of the fluid with surfaces of the sensor, or in the case of optical sensors, possibly with surfaces of vessels interposed between the fluid and the sensor. For optical sensing, over the course of hours of use of the sensor, an indicator generated by the reagent may build up on surfaces of the sensor or vessel facing the fluid, thereby affecting the optical absorbance detected by the sensor and causing drift of measurements. As a result of this problem, various sensors of this type currently commercially available require frequent recalibration by the user, and their results are not considered sufficiently reliable as a basis for clinical decisions.

Finally, devices of this type are generally implemented as disposable devices which must be discarded after a few days of use. Since each device includes costly components of the sensor itself and the other electronic components required for operation, replacement of the device every few days renders it expensive for ongoing use.

Various features of the present invention are intended to address some or all of the above problems.

In the field of drug delivery devices, US Patent Application Publication No. 2003/0216683 discloses a particularly advantageous fluid delivery system which achieves precise control over very low dosage delivery from a pressurized reservoir by employing a combination of two valves and a flow restriction, together with pressure measurement. The desired quantity is delivered as a sequence of variable duration intermittent pulses of fluid flow.

SUMMARY OF THE INVENTION

The present invention is a system for monitoring of metabolite concentration within a human or animal body.

According to the teachings of the present invention there is provided, a metabolite monitoring system comprising: (a) a microdialysis probe including a semi-permeable membrane and a probe flow path passing from an inlet through a sensing volume adjacent to the semi-permeable membrane to an outlet; (b) a fluid delivery device for delivering dialysate to the inlet; and (c) a metabolite monitoring system associated with the outlet for monitoring a concentration of at least one metabolite in the dialysate from the microdialysis probe, wherein the fluid delivery device is configured to deliver a pulsed flow of the dialysate to the inlet.

According to a further feature of the present invention, the fluid delivery device includes: (a) a pressurized reservoir containing a quantity of the dialysate; (b) at least one valve deployed for selectively opening and closing a supply flow path from the pressurized reservoir to the inlet; and (c) a control system associated with the at least one valve and configured to selectively open the at least one valve to allow pulsed flow of the dialysate to the inlet.

According to a further feature of the present invention, the fluid delivery device further includes: (a) a flow restrictor deployed in the supply flow path; and (b) a pressure measurement arrangement associated with the control system and deployed to measure a pressure drop across at least part of the flow restrictor.

According to a further feature of the present invention, the microdialysis probe has an operative volume, and wherein each pulse of the dialysate delivered to the inlet has a volume less than the operative volume of the microdialysis probe.

There is also provided according to the teachings of the present invention, a metabolite monitoring system comprising: (a) a microdialysis probe; (b) a dialysate delivery arrangement for generating flow of a dialysate into and out from the microdialysis probe; and (c) a reagent delivery arrangement for supplying a reagent for mixing with the dialysate from the microdialysis probe, wherein the reagent delivery arrangement and the dialysate delivery arrangement each includes a fluid reservoir acted upon by a piston to deliver the fluid, wherein the reagent delivery arrangement and the dialysate delivery arrangement are mechanically linked so as to maintain a fixed ratio between a quantity of dialysate delivered and a quantity of reagent delivered.

According to a further feature of the present invention, a first of the reagent delivery arrangement and the dialysate delivery arrangement includes a flow control system having at least one control valve, and wherein closure of the flow control valve stops fluid delivery from the other of the reagent delivery arrangement and the dialysate delivery arrangement due to the mechanical linkage.

According to a further feature of the present invention, the fluid reservoirs of the reagent delivery arrangement and the dialysate delivery arrangement are substantially concentric fluid reservoirs.

According to a further feature of the present invention, the substantially concentric fluid reservoirs are at least partially enclosed between opposing overlapping piston elements such that relative axial displacement of the overlapping piston elements generates delivery of the dialysate and the reagent in the fixed ratio.

There is also provided according to the teachings of the present invention, a sensor arrangement for sensing optical transmission through a water-based solution, the sensor arrangement comprising: (a) a measurement cell having an inner volume for receiving a quantity of the solution, the measurement cell having an inlet, an outlet and an additional opening, the additional opening being provided with at least one selected from of the group consisting of: hydrophobic surfaces to inhibit escape of the solution through the additional opening; and an open area smaller than an open area of the outlet; (b) a radiation source for directing optical radiation in through a first of the outlet and the additional opening so that radiation passes into the inner volume without passing through any surface in contact with the solution; and (c) an optical sensor deployed for sensing optical radiation passing out through a second of the outlet and the additional opening so that radiation from the inner volume reaches the optical sensor without passing through any surface in contact with the solution.

According to a further feature of the present invention, the inner volume is elongated from a first end to a second end, the inlet and the additional opening being located adjacent to the first end, and the outlet being located adjacent to the second end such that, when a new sample of solution is provided via the flow supply, the new sample of solution passes along the elongated inner volume from the first end to the second end displacing a previous sample of the solution.

According to a further feature of the present invention, there is also provided an absorbent medium deployed in proximity to the outlet without obstructing a light path passing through the outlet, the absorbent medium being configured for absorbing drops of the previous sample of the solution as they are released from the outlet.

According to a further feature of the present invention, the radiation source and the optical sensor are implemented as part of an electronics unit, and wherein the measurement cell is implemented as part of a disposable unit, the disposable unit being releasably engaged with the electronics unit so that the radiation source, the optical sensor, the outlet and the additional opening are aligned.

According to a further feature of the present invention, the outlet and the additional opening are aligned between the radiation source and the optical sensor.

According to a further feature of the present invention, there is also provided a microdialysis probe in fluid connection with the measurement cell.

There is also provided according to the teachings of the present invention, a metabolite monitoring system comprising: (a) a microdialysis probe; (b) a fluid delivery device for generating flow of a dialysate into and out from the microdialysis probe; (c) a flow path arrangement associated with the microdialysis probe and configured for receiving dialysate flowing out from the microdialysis probe, the flow path arrangement including: (i) a measuring cell having a contained volume, an inlet in fluid communication with the microdialysis probe, and an outlet, and (ii) an absorbent material deployed adjacent to the outlet so as to absorb dialysate passing out through the outlet; and (d) an optical sensor deployed for sensing optical properties of fluid contained within the contained volume, wherein the optical sensor does not come into contact with the fluid within the measuring cell.

There is also provided according to the teachings of the present invention, a metabolite monitoring system comprising: (a) a microdialysis probe; (b) a fluid delivery device for generating flow of a dialysate into and out from the microdialysis probe; (c) a flow path arrangement associated with the microdialysis probe and configured for receiving dialysate flowing out from the microdialysis probe, the flow path arrangement including: (i) a measuring cell having a contained volume, an inlet in fluid communication with the microdialysis probe, and an outlet, and (ii) an absorbent material deployed adjacent to the outlet so as to absorb dialysate passing out through the outlet; and (d) an optical sensor deployed for sensing optical properties of fluid contained within the contained volume, wherein the flow path arrangement is part of a disposable unit, and wherein the optical sensor is part of a reusable unit, the disposable unit and the reusable unit being configured to releasably interlock so as to produce a predefined spatial relation between the measuring cell and the optical sensor.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a system for monitoring of metabolite concentration within a human or animal body, and various components of such a system.

Before addressing the drawings, by way of a general introduction, the systems of the present invention are believed to have four primary sets of features, each of independent utility and patentable significance in its own right, which may be combined in synergy to provide further advantageous configurations of the present invention. These four primary sets of features will first be set out briefly below, followed by a more extensive description of one particularly preferred embodiment of the invention which implements all four of these sets of features. Although primary emphasis will be placed on these four sets of features, it should be noted that this emphasis is not intended to negate the patentable significance of various other significant features described below, even where they do not fall into one of these four categories.

Pulsed Delivery of Dialysate

In order to achieve consistent and accurately regulated flow through the microdialysis probe, it is a particularly preferred feature of certain implementations of the present invention that dialysate fluid, preferably isotonic saline solution, is delivered to the probe in small pulses of fluid flow. The volume of each pulse may be significantly less than the volume of fluid in the operative volume (i.e., the volume in contact with the probe membrane) at any given time. In this case, the sample of fluid leaving the probe in each pulse is assumed to be indicative of the metabolite concentration in the surrounding body fluid at the time it leaves the probe. In the particularly preferred example described below, a dialysate pulse volume of 0.1 micro-liter, once per minute, was used. Since, however, this volume is delivered in the form of a short pulse with an instantaneous flow rate much greater than the average flow rate, reliable and repeatable control of the flow is achieved.

Parenthetically, it should be noted that the dialysate solution does not necessarily, or even typically, reach full equilibrium of metabolite concentration with the surrounding body fluid. Nevertheless, since the diffusion conditions (fluid pulse volume and rate) remain constant, the concentration of metabolite in the dialysate exiting the probe is directly related in a consistent manner to the concentration in the body fluid, and allows determination of the body fluid concentration through an initial calibration procedure, as described in below. In certain preferred cases, the dwell time of the fluid within the probe and the probe design itself are chosen such that the concentration of metabolite in the dialysate does closely approach equilibrium conditions, i.e., equal concentration with the surrounding body fluid.

A fluid delivery device particularly suitable for controlling fluid dosage values of these orders of magnitude delivered in pulses is described in US Patent Application Publication No. 2003/0216683 which is hereby incorporated in its entirety by reference. An implementation of the invention employing a fluid delivery device based upon the teachings of the aforementioned publication will be described below.

Parallel Flow Control by Single Flow Regulation

A further particularly preferred feature of certain implementations of the present invention is that a single flow regulation arrangement is used to regulate the flow of two separate fluids, the dialysate and a reagent solution employed in the measurement process. This achieves significant simplification of the fluid flow regulation system, and ensures a constant ratio between the two fluid flows without requiring complicated coordination.

The parallel control is preferably achieved by providing one or more double-reservoir structure in which two fluid storage chambers are acted on by a corresponding pair of pistons. The two fluid supply arrangements are mechanically linked so as to move together. This mechanical linkage ensures that, under all conditions, fluid supply rates from the two reservoirs remain in a given preset ratio. Thus, accurate regulation of one flow rate is effective to regulate both fluid flows.

In the particularly preferred implementation illustrated below, the pistons are spring-biased to apply pressure to the reservoirs, thereby tending to deliver fluid along the two fluid flow paths. One of the flow paths is regulated with a system of valves etc. as will also be described below, such that the regulated fluid itself prevents motion of the piston between pulses. Because of the mechanical linkage, the second piston is also prevented from moving and no fluid flows in either flow path. Most preferably, as an added precaution to ensure sterility, one or more simple one-way valve ("check valve") may be included to preclude reverse flow or diffusion.

Non-Contact Optical Sensing

A further particularly preferred feature of certain implementations of the present invention relates to an arrangement and corresponding method for performing optical sensing of the properties of the sample fluid (mixed dialysate and reagent) in which components of an optical sensor measure the properties of the sample fluid within a measurement cell without the sensor components coming into contact with the fluid. In certain particularly preferred implementations, light from a source of radiation passes through the fluid and reaches a radiation sensor without passing through any surface which is in contact with the fluid. This has profound advantages in terms of uniformity of measurements since it avoids problems associated with build-up of substances on the vessel walls or sensor surfaces over the period of use of the device. It should be noted that this aspect of the invention in particular is considered to be applicable to a wide range of other applications in which any water-based solution is to be analyzed by transmission of optical radiation.

In general terms, the sensor arrangement according to this aspect of the present invention includes a measurement cell having an inner volume for receiving a quantity of the solution, the measurement cell having an inlet, an outlet and an additional opening. Preferably, the additional opening is provided with hydrophobic surfaces to inhibit escape of the solution through the opening. Additionally, or alternatively, the additional opening is formed with an open area smaller than that of the outlet. As a result of one or both of these features, together with proximity of an absorbent material (e.g., porous synthetic sponge material) to the outlet, fluid introduced through the inlet passes along through the measurement cell without exiting the additional opening and instead exits from the outlet.

By aligning the outlet and the additional opening, it is possible to perform transmission optical testing of a sample within the measurement cell without the radiation passing through any surface in contact with the liquid. This results in more reliable and consistent measurements than are achieved by conventional "contact" sensors in which the liquid comes in contact directly with the sensor.

Parenthetically, although described herein in the context of one particularly preferred implementation employing an optical transmission sensor system, it should be noted that the other features of the invention may also be implemented in the context of other measurement systems, for example, an optical sensor system measuring back-scattered radiation intensities.

Subdivision of Components

Finally, it should be noted that the components of the system of the present invention are preferably subdivided between a disposable portion and a reusable portion, as will be described below. Specifically, all parts coming in contact with the fluids, including the reservoirs, tubing, measuring cell and absorbent material, are all included in the disposable unit for use during a single monitoring session (typically a few days) and are then discarded. The optical sensor components, on the other hand, and preferably all of the electronic components of the system, are included in a reusable unit which mates with the disposable unit.

Figure 12:
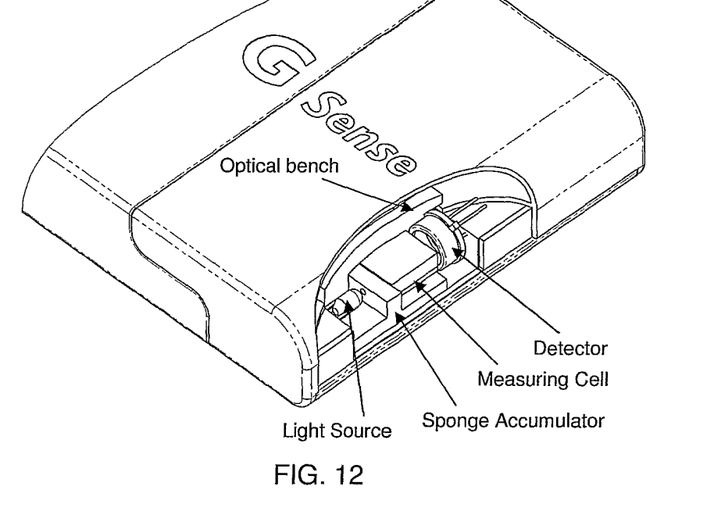
FIG. 12 is a partially cut-away view of the assembled system of FIG. 3B illustrating the alignment when engaged of a measurement cell of the disposable unit with components of an optical sensor arrangement of the reusable unit.
Figure 13:
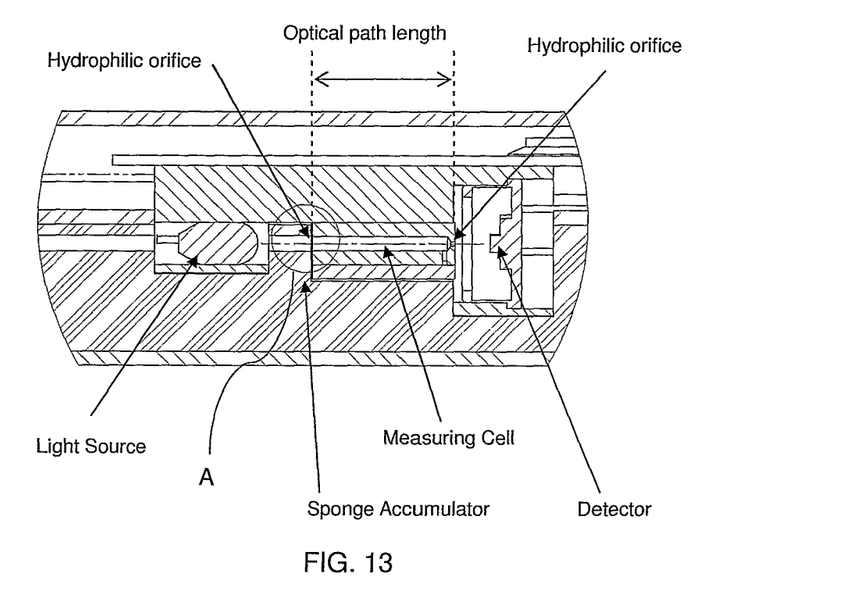
FIG. 13 is an enlarged cross-sectional view taken along the optical sensor axis of FIG. 12.
Figure 14:
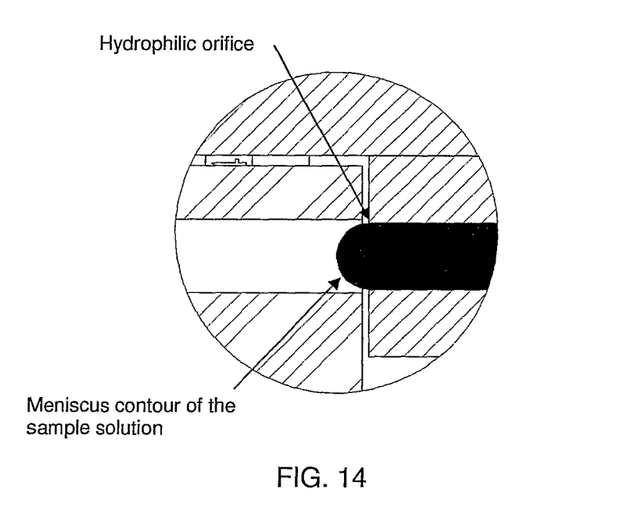
FIG. 14 is an enlarged view of the region of FIG. 13 denoted "A".

A preferred implementation for achieving correct spatial relation between the measuring cell and the optical sensor components will be described below with reference to FIGS. 12 and 13. Interconnections between other electronic components in the reusable unit and corresponding elements associated with the flow path in the disposable unit, such as for control of valves and measurement of fluid pressure, may be implemented according to the teachings of US Patent Application Publication No. 2003/0216683 and PCT Patent Application Publication No. WO03/045302.

DETAILED EXAMPLE

Figure 1:
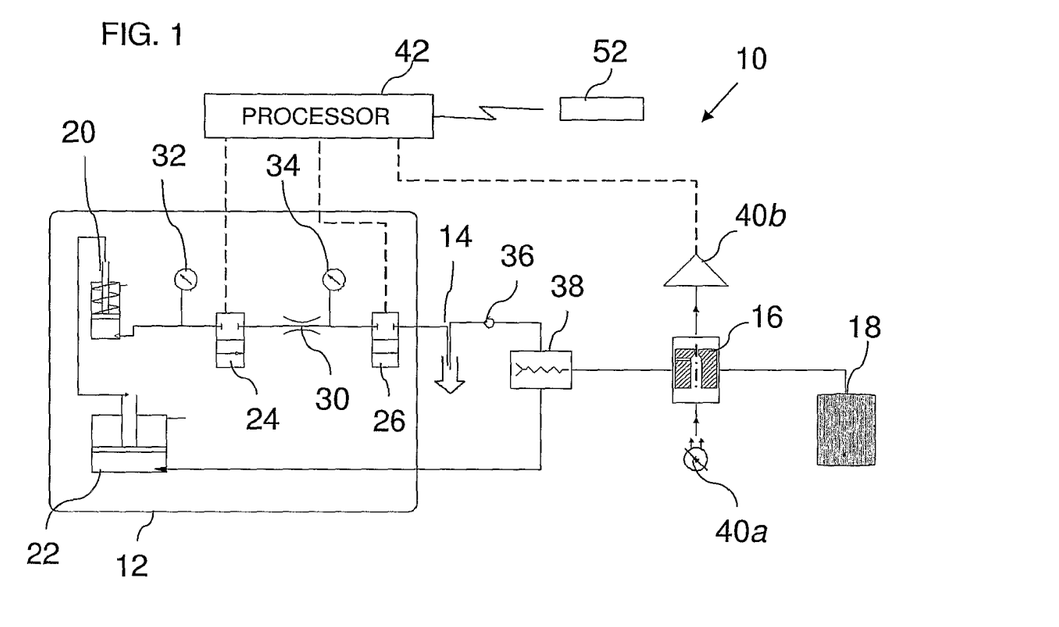
FIG. 1 is a schematic representation of a metabolite monitoring system, constructed and operative according to the teachings of the present invention.
Figure 2:
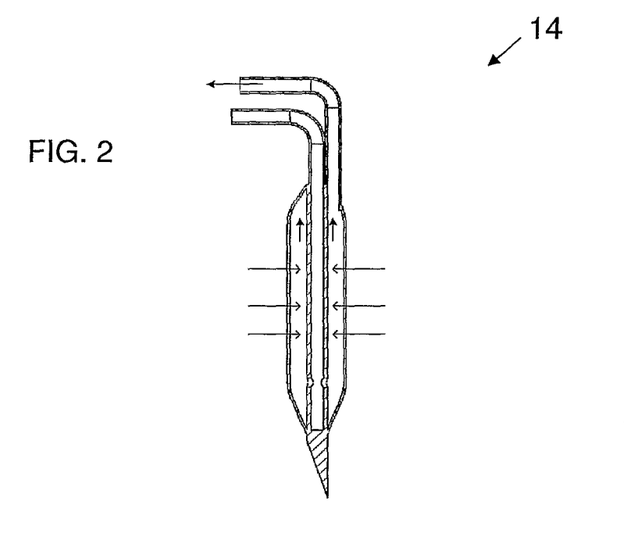
FIG. 2 is a schematic cross-sectional view of a microdialysis probe for use in the system of FIG. 1.
Figures 3A, 3B:
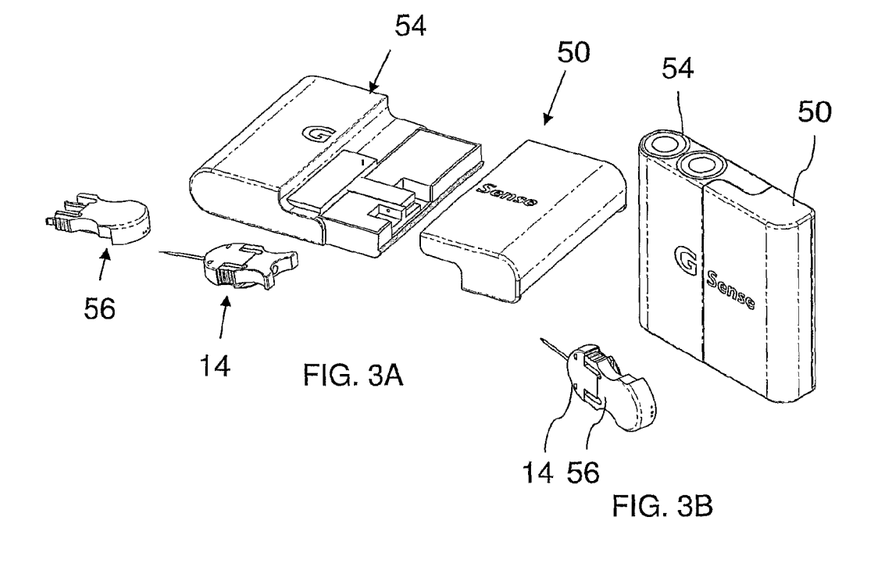
FIGS. 3A and 3B are schematic isometric views of an implementation of the system of FIG. 1 employing a disposable unit and a reusable unit, shown prior to interconnection and after interconnection, respectively.

FIG. 1 is a block diagram that illustrates the overall structure of a preferred implementation of a system, generally designated 10, constructed and operative according to the teachings of the present invention. The physiological saline is transferred from the cartridge 20 that serves as a pressure source for the flow of the solution, through the first valve (valve 1) 24, the restrictor 30 and the second valve (valve 2) 26 to the probe 14 in the tissue, shown in more detail in FIG. 2. In the probe 14, the equalization process is accomplished between the glucose from the interstitial fluid to the solution in the membrane.

From the probe 14, the solution flows through a non return valve 36 to the mixing cell 38. There the flow of the solution is mixed with the reagent flow and they start to interact. The reagent may be, for example, a color indicating reagent that contains Glucose oxidase which is an enzymatic reagent (available commercially from Raichem, (San Diego, Calif.), as Glucose color reagent catalogue no. 80038) that reacts with glucose to generate a color corresponding to an absorption around 500 nm wavelength. The color effect is proportional to the glucose level; the higher the concentration in the solution, the darker the color of the solution in the measurement cell. The solution exits from the mixing cell 38 and arrives a few minutes later (depending on the flow rate) to the measurement cell 16. The light source (UV/VIS) 40a and the detector (UV/VIS) 40b are deployed on opposite sides of the measurement cell 16. The absorbance measurements are used to calculate the glucose concentration in the solution. Due to the structure of the measurement cell 16, as further illustrated in FIGS. 9, 12A, 12B and 13, the solution tends to flow along the cell and exit from the larger opening near the sponge. The capillarity action of the sponge causes it to act as a liquid "sink", absorbing the solution that exits from the measurement cell and comes in contact with the sponge. Thus the old solution is removed from the cell and a new sample of the solution is presented to the sensor.

The pressure sensors 32 and 34 measure the pressure drop across the flow restrictor 30 and the first valve 24, providing information used to control dosing and schedule the solution flow rate with the help of the valve. Processing of the optical sensor data to calculate the glucose concentration and control of the valve and the flow rates is done by a micro processing and control unit. The display of the concentration and direction of variation of glucose, and user operation of the device are provided by the user interface.

Physically the system is preferably assembled from four main parts (FIGS. 3A-4B):

1. Measuring and control (Reusable) Unit 50—measurement and control system (FIG. 3A) that includes: the optical measurement system component 40a, 40b; a microprocessor 42 that controls the physiological saline dose and calculates the concentration in the interstitial fluid; and most other electronic parts of the system.
2. User interface 52 (shown schematically in FIG. 1) that includes a display of the concentration and direction of variation of glucose in the interstitial fluid and a few pushbuttons used to control the device. Communication between the Measuring and Control Unit and the User Interface is most preferably implemented by wireless communication, such as by a RF Bluetooth standard receiver/transmitter.
3. Disposable Unit 54—single use system (FIG. 5), which must be replaced every 4 days of use, includes all parts that come in contact with the physiological saline: a pump 12 that includes: a double cartridge (pressurized) each combining a cartridge 20 for saline with another concentric cartridge 22 for reagent; the valve system including valves 24, 26; restrictor 30; pressure sensors 32 and 34; the measurement cell 16; and the sponge 18 in which the solution is collected after use. Furthermore, this unit contains the power source for the entire system and output components that work on high voltage to operate piezoelectric actuators of the valves. From this unit, three fine tubes exit to a connector 56 that connects to the probe 14 by needles that penetrate into a suitable interface. One tube carries physiological saline, the second carries the reagent, and the third returns the mixed solution to the measurement cell in the Disposable Unit 54. In the particularly preferred implementation illustrated here, as best seen in FIG. 8B, the connector 56 contains the mixing cell 38 and conduits that carry the different solutions: physiological saline without glucose to the probe; diffused glucose solution from the probe to the measuring cell; reagent solution from the cartridge to the mixing cell, and, mixed solution from the mixing cell to the measuring cell.
4. Probe 14—the probe and the instruments that are used to insert it into the tissue.

These four main components, and their sub-components, will now be described in more detail.

User interface 52—the communication between the sensor and the user is conducted via a separate User interface that include a display (LCD) to show the concentration and direction of variation (increasing or decreasing) of glucose in the interstitial fluid and a few push-buttons used to control the device.

Figure 4A:
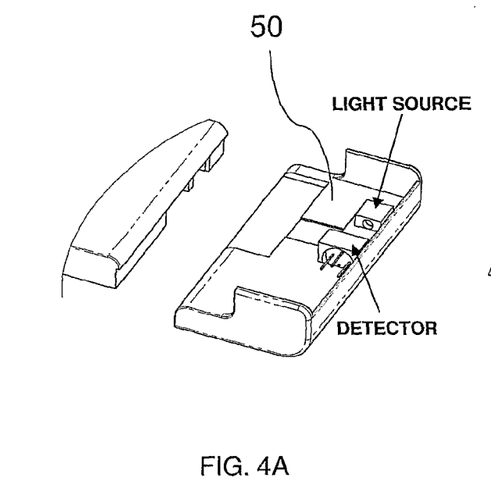
FIGS. 4A and 4B are schematic lower and upper isometric views of the reusable unit from the system of FIG. 3A.
Figure 4B:
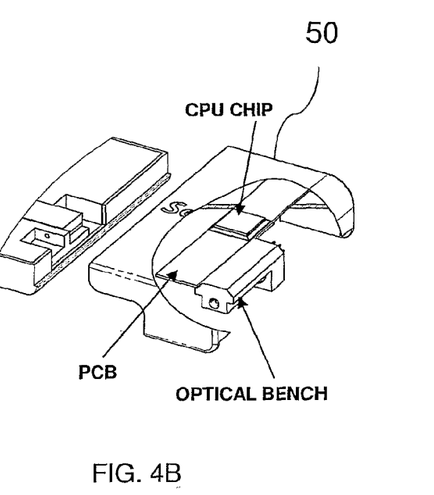

Measuring and Control Unit—(FIG. 4A, 4B). This unit executes the measuring and control operations of the system: it measures the absorbance spectrum through an optical measuring unit (light source and detector) which are installed therein and employs the microprocessor to calculate the concentration of glucose in the interstitial fluid. This unit reads the voltage signal from the pressure gauge and uses the information to command the valve actions to ensure the precise timing of the solution flow in the probe and the mixing cell.

The Measuring and Control Unit also preferably provides a communication link between sensor system and the User Interface by a RF receiver/transmitter. The Measuring and Control Unit is typically implemented as a base installed with a card that contain the electronics and PCB connectors, a case that contains the optical bench of the measuring system and a rigid plastic shell that connects to the Disposable Unit.

The base fixes the positions of the electronic card and the optical bench, and carries on them the electric parts and electro optics which are used in the measuring unit and all the parts that are used to control the solution flow rate. These components include low voltage power components of the valve, the power components of the pressure sensor and other logical components that are used to implement the sequence of operations performed by the system. The sub-components of the measuring system are the output components and light source logical components, the light source, the detector and all the logical components (e.g. microprocessors) that are used to process from the detector and implement the system algorithms. The connection of the power source, pressure sensor in the Disposable Unit, and the components in the Measuring and Control Unit is done by a connector.

The optical components e.g. lenses, grating and/or filters, the window, the light source, and the detector are found in the optical casing which ensures rigid and accurate relative positioning of these components. The Measuring and Control Unit closes by a cover that provides complementary and/or interlocking features that allow engagement of the unit with the Disposable Unit of the system.

Disposable Unit—(FIG. 5) The Disposable Unit performs a number of functions: it infuses the physiological saline in precise amounts and timing to provide a repeating dosage to the membrane where the concentration interchange with the interstitial fluid occurs; it mixes the fluid which has passed through the probe with a constant ratio of reagent; delivers it to the measurement system; and finally, stores the fluid after use. Since the unit contains all the components that come into contact with the physiological saline and/or the user's body, it is implemented as a disposable unit to ensure hygiene and sterility. The Disposable Unit cannot be used by the patient for more than four days (96 hours) because the probe (adapted in the tissue) might cause inflammatory reaction in the insertion point if left in place too long. Since this unit has a one time use, its manufacture cost has critical importance for economic reasons.

Figure 6:
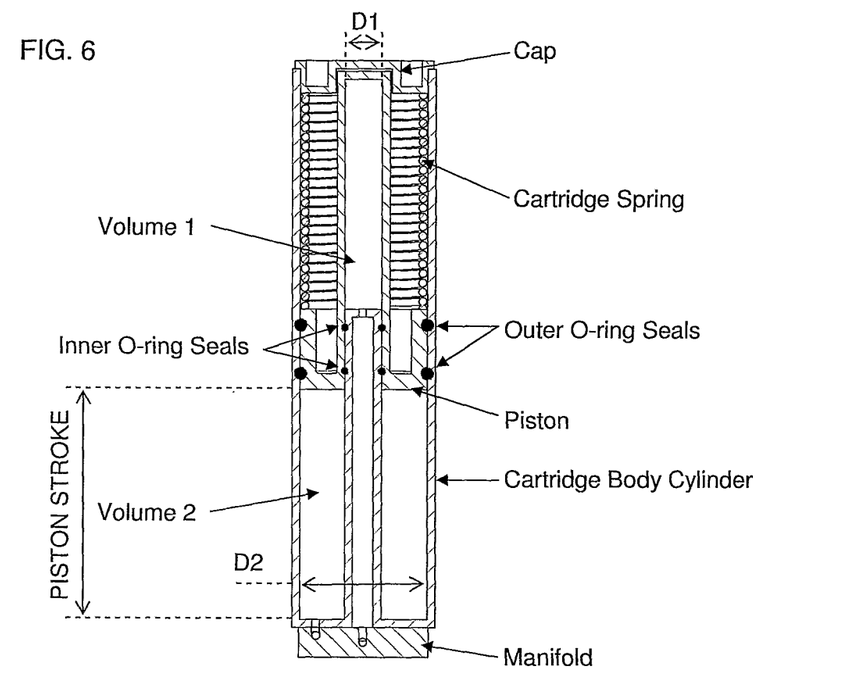
FIG. 6 is a schematic isometric view of a pressurized fluid reservoir from the disposable unit of FIG. 5.

The unit is built of a base that consists as a reservoir/source of pressure for the physiological saline. The energy to generate the pressure for the flow is stored in the cartridge spring which presses from one side on a hydraulic piston with a valve (cartridge piston) and on the other side is loaded by a screw-nut installed on the base. The hydraulic piston presses the solution and forces it to flow toward the probe when the first valve (valve 1) opens. The base contains two pressure reservoirs like this. Every pressure reservoir, double cartridge (FIG. 6) is preferably made of two concentric volumes with a constant ratio between them (actually a double piston). The small volume contains the physiological saline and the bigger one (typically the external one) contains the reagent. Movement of the piston, occurring on opening of the valves controlling flow of the physiological saline, also results in release of the reagent in fixed volumetric ratio to the saline.

The valve unit (FIG. 7) is located on the base and connected to the pressure reservoir by tubing. The valve unit contains the first and second valves (valve 1, valve 2), the manifold that connects between the valves and contains the restrictor, and a connecting point for the tubing that leads the solution to the probe. Two pressure transducers are installed from both sides of the restrictor. The Measuring and Control Unit processes signals from the pressure transducers to determine the flow rate of the physiological saline in the restrictor. These valves are activated by PZT actuators which are controlled by the Measuring and Control Unit.

Figure 7:
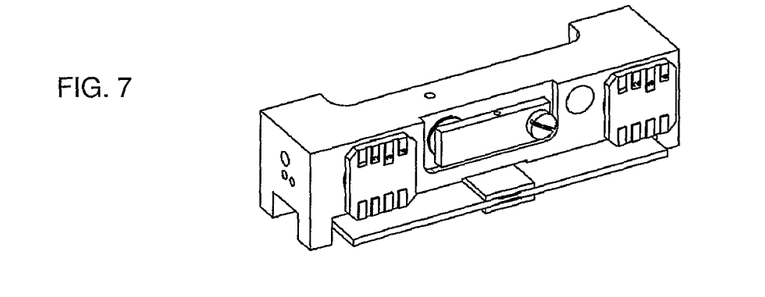
FIG. 7 is a schematic isometric view of a flow control valve block from the disposable unit of FIG. 5.

The Valves Block is typically assembled from the following parts:

A micro injection Block.
Two control valves.
A Glass restrictor.
Two absolute pressure sensors.
Two PZT actuators ("benders").

All three valves preferably work as normally-closed (N.C.) valves (when their benders are preloaded). The valve actuators are controlled by 150V pulses. The valves themselves are preferably formed from a 1 mm pin, a thin elastomer (0.1 mm) and a bushing.

Figure 5:
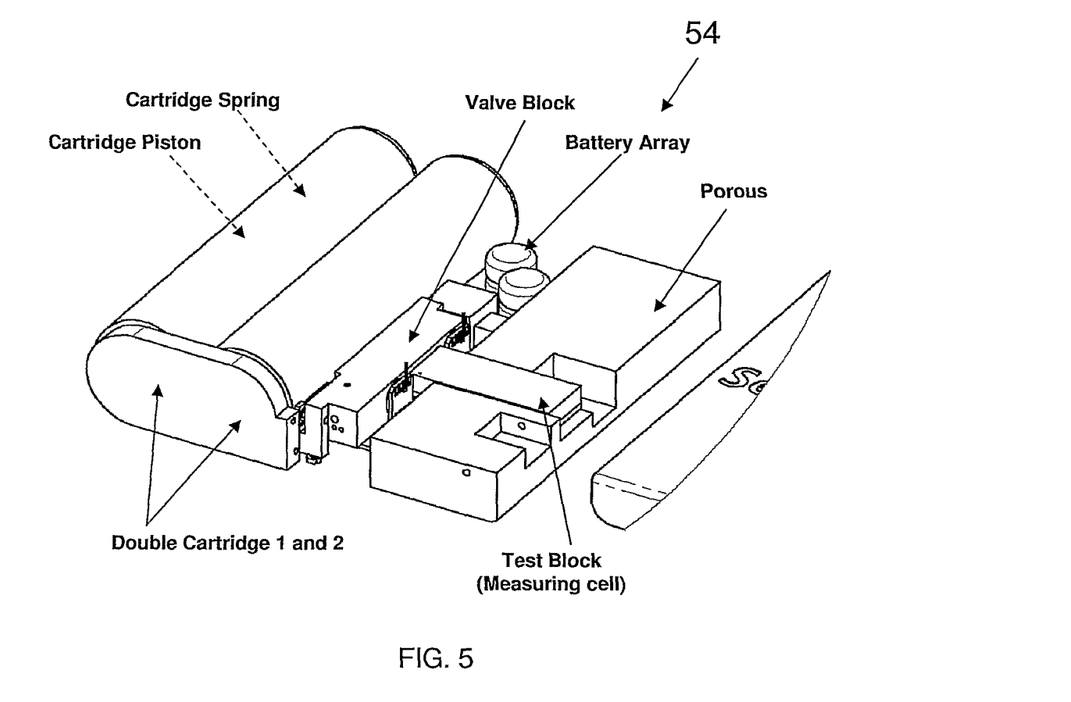
FIG. 5 is an isometric view of the disposable unit from the system of FIG. 3A.

Also located on the base are a power source (battery) which provides the power to activate the system and various components which operate at high voltage (150V) for operating the PZT actuators. The Disposable Unit is closed by a cover that contains the locking mechanism of the Measuring and Control Unit, and additional complementary and/or interlocking features provide precise alignment of the relative positions of the two units.

Figure 8A:
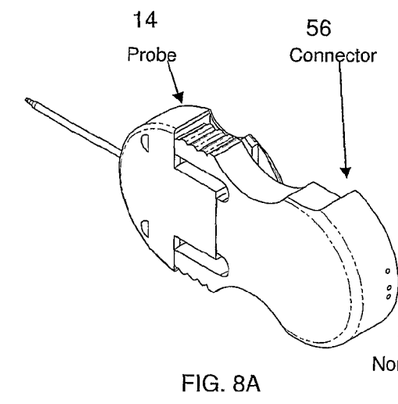
FIG. 8A is a schematic isometric view of a microdialysis probe implementation from the system of FIG. 3A.
Figure 8B:
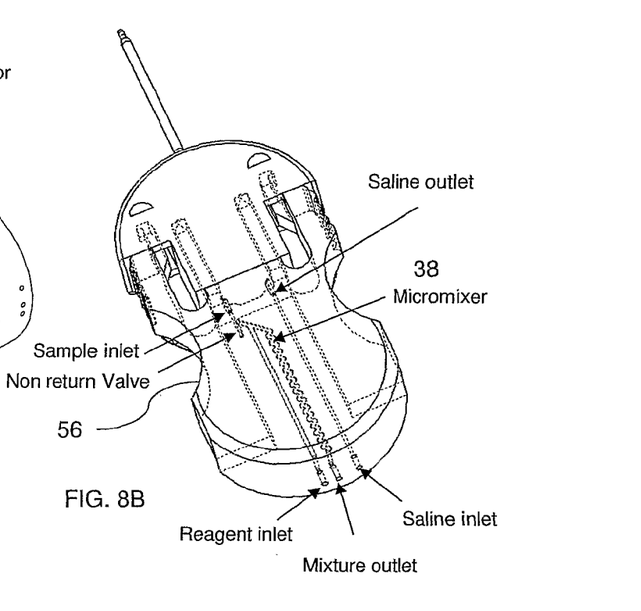
FIG. 8B is a partially cut-away enlarged view of a part of the microdialysis probe of FIG. 8A showing an internal structure of a connector used with the probe.

In addition, a section of flexible tube extends from The Disposable Unit to a connector that connects it to the probe (FIGS. 8A-8B). The tube, typically of length around 100 mm, contains three separate lumens or passageways carrying: physiological saline to the probe; reagent solution on the way to the mixing cell; and a mixed solution of reagent-sample from the mixing cell back to the measurement cell within the Disposable Unit. Altogether, the connector has 3 inlets (physiological saline, reagent solution and a sample from the probe) and two outlets (physiological saline to the probe and a reagent-sample to the measurement cell). The inlets and outlets to and from the probe are preferably implemented as small needles imbedded in the appropriate interfaces. The entry of the sample from the probe contains a miniature non return valve, which prevents from the sample flowing back and the reagent entering the probe. The sample from the probe and the reagent feed into the mixing cell—a miniature labyrinth section, and from there, the mixture passes back along the flexible tube to the measuring cell (FIG. 9) located inside the Disposable Unit itself.

Probe infusion set—this is a separate disposable arrangement that includes the probe for insertion into the tissue and protective covering for protecting the probe prior to use (FIGS. 10A-11B).

Operation:

1. Installation and Removal:

First, the user activates the sensor system by connecting the Measuring Unit to The Disposable Unit. Afterward the probe is inserted to the tissue and the needle inside the cannula is removed, leaving only the flexible probe in the tissue. Then, he or she attaches the connector of the Disposable Unit to the probe. The user carries the device on a belt or by any other suitable form of attachment to his body. The user interface is preferably carried on a strap attached to his wrist (like a watch). The user can disconnect the probe from the sensor at the connector, to be able to take a shower, or for swimming and like. After 96 hours, the user extracts the probe from the tissue, removes the device of his body and then, separates the Disposable Unit from the Measuring Unit, discards the Disposable part and installs a new one in its place. In FIG. 12, the location of the light source and the sensor can be observed inside the optic bench on the reusable part next to the measuring cell, and the sponge can be seen as part of the Disposable part.

2. Set-Up Phase:

The system set up is carried out automatically on activation of the system. In the initial phase, valve 1 and 2 are closed, and the solution is kept at a pressure of about 5 bar in the pressurized source.

After installation, the system executes a priming set up—rinsing the pipeline with the different solution, physiologic, reagent and mixed, in order to extract any air bubbles. The rinsing is conducted by opening the two valves for a sufficient amount of time to fill the entire pipeline.

The rinsing delivers quickly solution through the probe. As a result, the solution doesn't undergo diffusion with the tissue, and doesn't include any glucose. As a result, mixing of the saline and reagent does not result in a color reaction. In this phase, when the measuring cell is full of the mixing sample without glucose or reagent, the measuring unit executes relative measurement of the sensor reaction (I) when the light source is shut ($I_{Dark}$) and the sensor reaction with an open light source ($I_{Reference}$). These results are then used to calculate the Absorbance of the samples according to:

$$\text{Absorbance} = -\log\left(\frac{I - I_{dark}}{I_{reference} - I_{dark}}\right)$$

3. Generating a Reaction between the Physiological Saline and the Interstitial Fluid:

The micro pump is actuated to deliver the solutions in constant volumes. In the preferred example described herein, volumes of 0.1 uL of physiological saline and 2.4 uL of reagent solution are delivered every minute in pulses. The physiological saline flows longitudinally over the inner side of the probe. A segment of this side is a membrane that allows for glucose molecules to pass from the interstitial fluid outside, in contact with the outer side, to the physiological saline that flows inside.

It is assumed that glucose molecules diffuse also inside the pipeline so that the glucose concentration in the probe volume before the non-return valve is uniform, and can be taken as an indication of the glucose concentration in the interstitial fluid over the minute prior to it exiting the probe. In this example, the volume within the probe is significantly bigger than the solution doses that are delivered each minute. As a result, each pulse of dialysate remains within the probe volume for several minutes, thereby allowing the glucose concentration within the saline to get closer to equilibrium than would be achieved by more rapid fluid exchange. Since one dose is delivered every minute, each pulse volume that exits the non return valve contains the information of the glucose concentration in the probe volume lagging by one minute.

4. Glucose Concentration Measuring

After the solution dose passes the non return valve, it mixes with the reagent solution in the mixing cell so that the flow rate from the mixing cell to the measuring cell is one 2.5 uL pulse a minute. In the exemplary embodiment described herein, the fluid flow path is such that four minutes pass from the moment the solution passes the non return valve to the moment it finishes passing through the measuring cell (2 uL measuring cell volume and 8 uL pipeline volume). On the assumption that some diffusion of molecules occurs inside the pipeline, the glucose concentration in the tube beyond the non return valve may affect slightly the concentration in the measuring cell.

Figure 9:
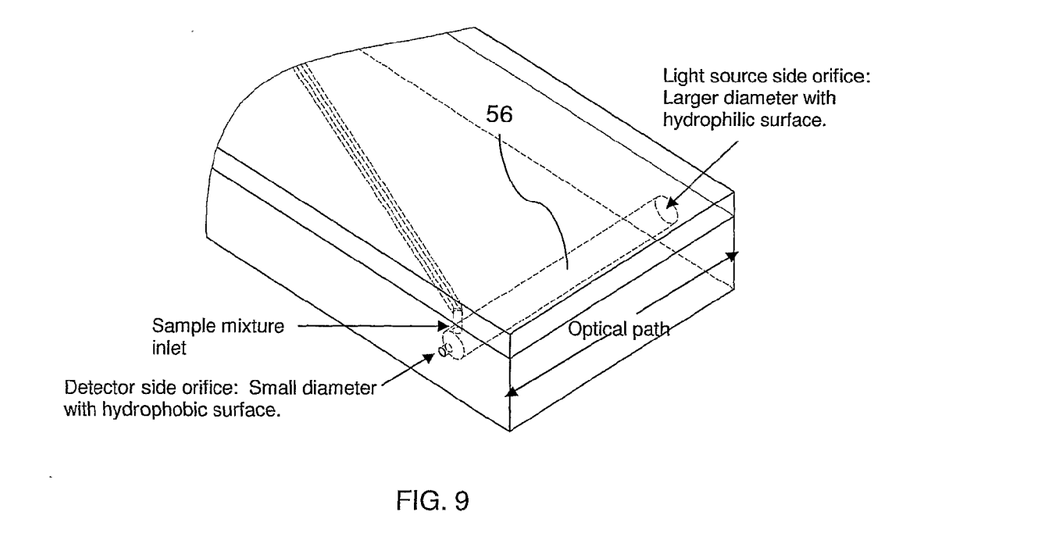
FIG. 9 is a schematic view of a measurement cell from the disposable unit of FIG. 5.
Figure 10A:
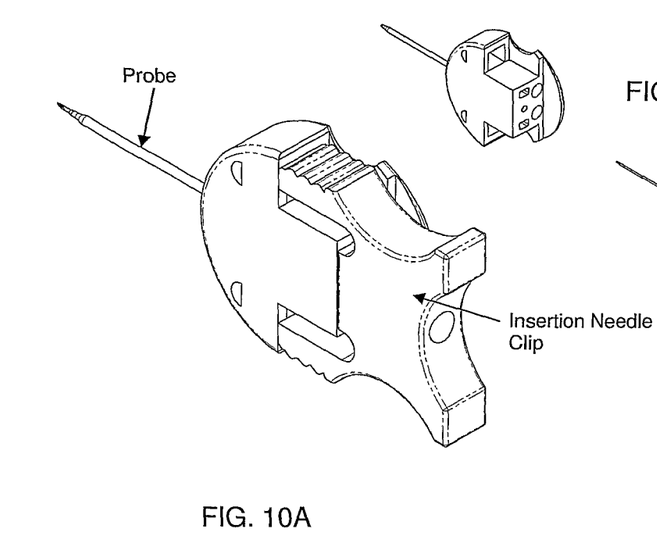
FIGS. 10A and 10B are schematic isometric views of the microdialysis probe of FIG. 8A shown with an insertion needle clip in its inserted and withdrawn positions, respectively.
Figure 10B:
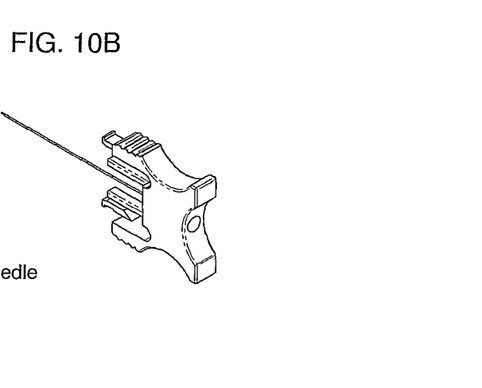
Figures 11A, 11B, 11C:
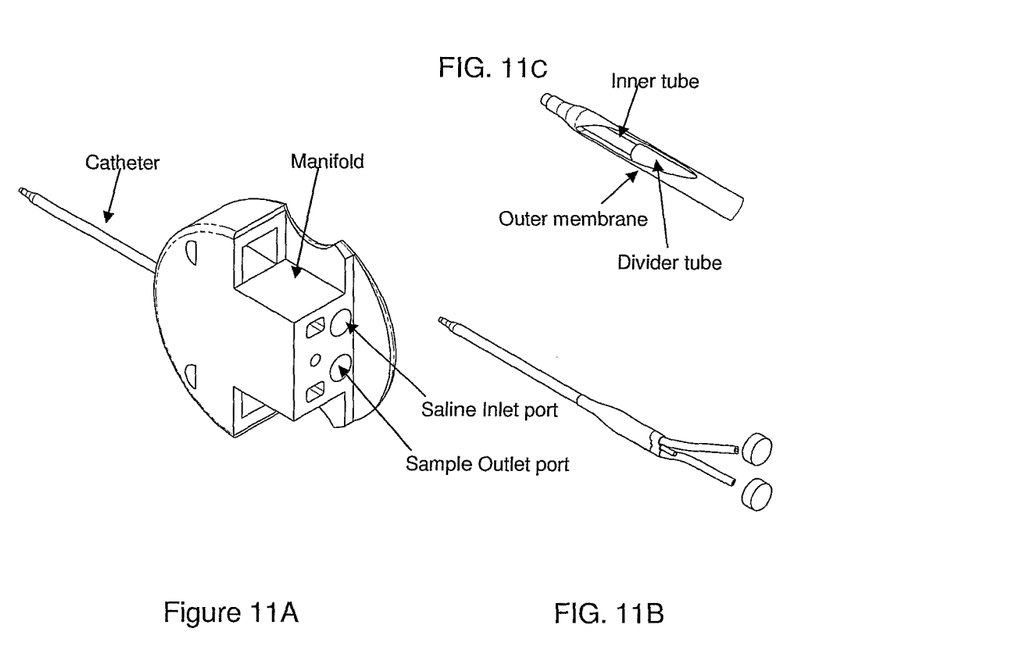
FIG. 11A is an enlarged, partially cut-away view of the microdialysis probe of FIG. 8A showing an inlet port, and outlet port and a flow path structure.
FIG. 11B is an enlarged view of the flow path structure from the microdialysis probe of FIG. 11A.
FIG. 11C is an enlarged view of the distal portion of the probe of FIG. 11A.

The glucose in the physiological saline reacts with the reagent. The reaction and with it the color are stabilized during the flow to the measuring cell. The solution is introduced into a cylindrical measurement cell of 0.5 mm diameter (FIG. 9). The two ends of the cell are open to air, one being 0.5 mm diameter and the other being smaller with only 0.3 mm diameter. In addition, the area of the small end, or at least the surfaces of the opening itself, are made of a hydrophobic (water repellant) material, such as Teflon, while the other the rest of the diameter and the second end are made of a hydrophilic substance (water attracting) such as glass. As a result, due to surface tension effects, excess fluid tends to overflow through the larger diameter opening. The solution is introduced via an inlet near the small diameter opening (see FIG. 9) and thus the solution flows along the entire length of the measurement cell towards the larger diameter exit, replacing the previous fluid sample. A porous sponge is located next to the opening. When the meniscus formed at the opening comes into contact with the sponge, a quantity of fluid is sucked up by the sponge through capillary action and is removed from the measurement cell.

As mentioned above, the ends of the measurement cell are open to air. The light source and the sponge are located at the larger opening and the light detector from the smaller opening. As a result of this design, the detector "sees" primarily light that passes directly through the cell without passing through any surface in contact with the liquid. Preferably, the geometrical arrangement of the openings and the measurement cell are implemented such that light that strikes and is reflected from the cell's walls cannot reach the detector. This arrangement enables the measurement of glucose level without any medium or vessel (other than air) between the sampled solution and the measurement apparatus.

The solution is presented to the measuring system that measures the optical absorption at specific wavelength(s) that are appropriate to the color of the reagent and calculate the concentration of the glucose in the sample. The calculation is accomplished by an algorithm based on the calibration model developed for the system. In general, the calibration model defines the sensors reaction to values that are used to calculate the glucose level in the solution.

The concentration measured in the measuring cell is actually an average of the last four minutes that passes until the actual measuring. If we add the one minute delay of the probe, we can say that the glucose level measure in the cell represents the glucose level in the tissue after a five minute delay. If we add to that the roughly 10 minutes delay between the tissue level and the blood level, we can say that the device can give the user a measurement of the glucose level in the blood with a 15 minute delay. FIG. 13 shows the measuring system.

5. Removing the Solution after Measuring.

The absorbent (sponge) material is preferably formed with a cylindrical channel adjacent to and aligned with the larger hole (outlet) of the measurement cell. This allows the light source (or alternatively, the sensor, or both) to be positioned opposite and aligned with the opening, while ensuring that the absorbent material is in close proximity to the outlet for promptly absorbing and soaking up droplets which attempt to form by generating an outwardly bulging meniscus.

6. Initial Manual Calibration.

After stabilization of the system, the user is required to perform an initial manual calibration. In this calibration, the user performs an analysis with a standard glucometer (stabbing the finger) and inputs the result to the device through the user interface. This result is then used to calibrate the device, and no further calibration is needed subsequently during ongoing monitoring of the glucose level in the user's blood. Since the continuous measuring operation in the device is done without any contact between the sample and the measuring instrument and since the physical conditions of the measuring instrument in relation to the sample are unchanged throughout, there is normally no need for any further calibration.

5. Measuring Result Display:

The system calculates the glucose level in the blood based on the level measured in the solution and the calibration results, and shows the result on the user interface display. Since the device measures the glucose level at constant intervals, it can calculate and present the rate of change of the glucose level and thereby provide the user with an indication of the direction of variation of the glucose level in his body. Furthermore, the device can estimate based on the accumulated result the future levels of the glucose if the user does not take any action like eating, insulin dosing or strenuous activity.

It will be appreciated that the above descriptions are intended only to serve as examples, and that many other embodiments are possible within the scope of the present invention as defined in the appended claims.

What is claimed is:

1. A metabolite monitoring system comprising:
   (a) a microdialysis probe including a semi-permeable membrane and a probe flow path passing from an inlet through a sensing volume adjacent to said semi-permeable membrane to an outlet;
   (b) a fluid delivery device for delivering dialysate to said inlet; and
   (c) a metabolite monitoring system associated with said outlet for monitoring a concentration of at least one metabolite in said dialysate from said microdialysis probe,
wherein said microdialysis probe has an operative volume, and wherein said fluid delivery device is configured to deliver a pulsed flow of said dialysate to said inlet such that each pulse of said dialysate delivered to said inlet has a volume less than said operative volume of said microdialysis probe,
   wherein said fluid delivery device includes:
   (a) a dialysate delivery arrangement for generating said pulsed flow of dialysate; and
   (b) a reagent delivery arrangement for supplying a reagent for mixing with the dialysate from said microdialysis probe,
wherein said reagent delivery arrangement and said dialysate delivery arrangement each includes a fluid reservoir acted upon by a piston to deliver the fluid, wherein said reagent delivery arrangement and said dialysate delivery arrangement are mechanically linked so as to maintain a fixed ratio between a quantity of dialysate delivered and a quantity of reagent delivered, and wherein said fluid reservoirs of said reagent delivery arrangement and said dialysate delivery arrangement are substantially concentric fluid reservoirs, said substantially concentric fluid reservoirs being at least partially enclosed between opposing overlapping piston elements such that relative axial displacement of said overlapping piston elements generates delivery of said dialysate and said reagent in said fixed ratio.

2. The metabolite monitoring system of claim 1, wherein said fluid delivery device includes:
   (a) a pressurized reservoir containing a quantity of said dialysate;
   (b) at least one valve deployed for selectively opening and closing a supply flow path from said pressurized reservoir to said inlet; and
   (c) a control system associated with said at least one valve and configured to selectively open said at least one valve to allow pulsed flow of said dialysate to said inlet.

3. The metabolite monitoring system of claim 2, wherein said fluid delivery device further includes:
   (a) a flow restrictor deployed in said supply flow path; and
   (b) a pressure measurement arrangement associated with said control system and deployed to measure a pressure drop across at least part of said flow restrictor.

4. The metabolite monitoring system of claim 1, wherein a first of said reagent delivery arrangement and said dialysate delivery arrangement includes a flow channel system having at least one control, and wherein closure of said flow control valve stops fluid delivery from the other of said reagent delivery arrangement and said dialysate delivery arrangement due to said mechanical linkage.

5. The metabolite monitoring system of claim 1, wherein said metabolite monitoring system includes:
   (a) a measuring cell having a contained volume, said measuring cell being in fluid communication with said outlet of said microdialysis probe; and
   (b) an optical sensor deployed for sensing optical properties of fluid contained within said contained volume,
wherein said optical sensor does not come into contact with the fluid within said measuring cell.

6. A metabolite monitoring system comprising:
   (a) a microdialysis probe including a semi-permeable membrane and a probe flow path passing from an inlet through a sensing volume adjacent to said semi-permeable membrane to an outlet;
   (b) a fluid delivery device for delivering dialysate to said inlet; and
   (c) a metabolite monitoring system associated with said outlet for monitoring a concentration of at least one metabolite in said dialysate from said microdialysis probe, said metabolite monitoring system including:
      (I) a measuring cell having a contained volume, said measuring cell being in fluid communication with said outlet of said microdialysis probe, said measuring cell having an inlet, an outlet and an additional opening, said additional opening being provided with at least one selected from of the group consisting of: hydrophobic surfaces to inhibit escape of the fluid through the additional opening; and an open area smaller than an open area of said outlet; and
      (II) an optical sensor deployed for sensing optical properties of fluid contained within said contained volume, said optical sensor including:
         (i) a radiation source for directing optical radiation in through a first of said outlet and said additional opening so that radiation passes into said contained volume without passing through any surface in contact with the fluid, and
         (ii) an optical sensor deployed for sensing optical radiation passing out through a second of said outlet and said additional opening so that radiation from said inner volume reaches said optical sensor without passing through any surface in contact with the fluid,
   and wherein said microdialysis probe has an operative volume, and wherein said fluid delivery device is configured to deliver a pulsed flow of said dialysate to said inlet such that each pulse of said dialysate delivered to said inlet has a volume less than said operative volume of said microdialysis probe.

7. The metabolite monitoring system of claim 6, wherein said contained volume is elongated from a first end to a second end, said inlet and said additional opening being located adjacent to said first end, and said outlet being located adjacent to said second end such that, when a new sample of fluid is provided via said inlet, the new sample passes along said elongated contained volume from said first end to said second end displacing a previous sample of the solution.

8. The metabolite monitoring system of claim 6, further comprising an absorbent medium deployed in proximity to said outlet without obstructing a light path passing through said outlet, said absorbent medium being configured for absorbing drops of the previous sample of the fluid as they are released from said outlet.

9. The metabolite monitoring system of claim 6, wherein said outlet and said additional opening are aligned between said radiation source and said optical sensor.

10. The metabolite monitoring system of claim 1, wherein said metabolite monitoring system includes:
  (a) a measuring cell having a contained volume, said measuring cell being in fluid communication with said outlet of said microdialysis probe; and
  (b) an optical sensor deployed for sensing optical properties of fluid contained within said contained volume,
wherein said flow path arrangement is part of a disposable unit, and wherein said optical sensor is part of a reusable unit, said disposable unit and said reusable unit being configured to releasably interlock so as to produce a predefined spatial relation between said measuring cell and said optical sensor.

11. A metabolite monitoring system comprising:
  (a) a microdialysis probe;
  (b) a dialysate delivery arrangement for generating flow of a dialysate into and out from said microdialysis probe; and
  (c) a reagent delivery arrangement for supplying a reagent for mixing with the dialysate from said microdialysis probe,
wherein said reagent delivery arrangement and said dialysate delivery arrangement each includes a fluid reservoir acted upon by a piston to deliver the fluid, wherein said reagent delivery arrangement and said dialysate delivery arrangement are mechanically linked so as to maintain a fixed ratio between a quantity of dialysate delivered and a quantity of reagent delivered
and wherein said fluid reservoirs of said reagent delivery arrangement and said dialysate delivery arrangement are substantially concentric fluid reservoirs, said substantially concentric fluid reservoirs being at least partially enclosed between opposing overlapping piston elements such that relative axial displacement of said overlapping piston elements generates delivery of said dialysate and said reagent in said fixed ratio.

12. The metabolite monitoring system of claim 11, wherein a first of said reagent delivery arrangement and said dialysate delivery arrangement includes a flow control system having at least one control valve, and wherein closure of said flow control valve stops fluid delivery from the other of said reagent delivery arrangement and said dialysate delivery arrangement due to said mechanical linkage.

* * * * *